US008314208B2

(12) United States Patent
Collins

(10) Patent No.: US 8,314,208 B2
(45) Date of Patent: *Nov. 20, 2012

(54) MICROWAVE ENHANCED N-FMOC DEPROTECTION IN PEPTIDE SYNTHESIS

(75) Inventor: Jonathan M. Collins, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 358 days.

This patent is subject to a terminal disclaimer.

(21) Appl. No.: 11/351,796

(22) Filed: Feb. 10, 2006

(65) Prior Publication Data

US 2007/0270573 A1    Nov. 22, 2007

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. ........................................ 530/335; 530/334
(58) Field of Classification Search ........................ None
See application file for complete search history.

(56) References Cited

U.S. PATENT DOCUMENTS

| | | | |
|---|---|---|---|
| 3,926,556 | A | 12/1975 | Boucher |
| 4,108,846 | A | 8/1978 | Meienhofer |
| 4,696,981 | A | 9/1987 | Harada et al. |
| 6,288,379 | B1 | 9/2001 | Greene et al. |
| 6,744,024 | B1 | 6/2004 | Hayes et al. |
| 6,809,190 | B2 | 10/2004 | Ikeda et al. |
| 6,858,434 | B1 * | 2/2005 | Williams ...................... 436/161 |
| 2002/0117498 | A1 | 8/2002 | Jennings |
| 2003/0089706 | A1 | 5/2003 | Jennings |
| 2003/0199099 | A1 | 10/2003 | King et al. |
| 2004/0020923 | A1 | 2/2004 | Collins et al. |
| 2004/0260059 | A1 | 12/2004 | Collins et al. |

FOREIGN PATENT DOCUMENTS

EP    1 491 552 A    12/2004

OTHER PUBLICATIONS

Collins et al. New Method for Solid Phase Synthesis using Microwave Energy. Jul. 22, 2003. Presented at the American Peptide Symposium, Boston, MA.. pp. 1-8.*
A. Kramer et al, "Synthesis and Screening of Peptide Libraries on Continuous Cellulose Membrane Supports"; Methods in Molecular Biology, vol. 87: Combinatorial Peptide Library Protocols; Humana Press, Inc.; Totowa, NJ; pp. 25-39, 1998.
Collins et al: "Optimization of Microwave Enhanced Solid Phase Peptide Synthesis," Biopolymers, vol. 80, No. 4, 2005, p. 532.
Wade et al: "Base-induced side reactions in Fmoc-solid phase peptide synthesis: Minimization by use of piperazine as N-alpha-deprotection reagent," Letters in Peptide Science, vol. 7, No. 2, Mar. 2000, pp. 107-111.
Murray et al: "Application of microwave irradiation to the synethsis of 14-Helical beta-peptides," Organic Letters, ACS, Washington, D.C., vol. 7, No. 8, Mar. 22, 2005, pp. 1517-1520.

European Search Report for Application EP 07102079, Completion Date of Search May 29, 2007, 3 pages.
Hui-Ming Yu et al., Enhanced Coupling Efficiency in Solid-Phase Peptide Synthesis by Microwave Irradiation, The Journal of Organic Chemistry, Aug. 28, 1992, pp. 4781-4785, vol. 57, No. 18, American Chemical Society 1992.
Mate Erdelyi et al., Rapid Microwave-Assisted Solid Phase Peptide Synthesis: Synthesis 2002, Aug. 22, 2002, pp. 1592-1596, No. 11.
Shui-Tein Chen et al., The Studies of Microwave Effects on the Chemical Reactions, Journal of the Chinese Chemical Society, 1997, pp. 169-182, vol. 44, No. 3.
Shui-Tein Chen et al., Enhancement of Chemical Reactions by Microwave Irradiation; Journal of the Chinese Chemical Society, 1991, pp. 85-91, vol. 38. No. 1; Only 1 page Abstract enclosed.
Hernando J. Olivos et al., Microwave-Assisted Solid-Phase Synthesis of Peptoids, Organic Letters, 2002, pp. 4057-4059, vol. 4, No. 23, 2002 American Chemical Society.
N.S. Rao et al., Microwave Assisted High Yielding Preparation of N-Protected 2-Deoxyribonucleosides Useful for Oligonucleotide Synthesis, Necleosides, Nucleotides & Nucleic Acids, 2002, pp. 393-400, vol. 21 (4&5), Marcel Dekker, Inc., New York.
Claire M. Coleman et al., Microwave Parallel Library Generation: Comparison of a Conventional-and Microwave-Generated Substituted 4(5)-Sulfanyl-1H-imidazole Library, J. Comb. Chem., 2002. pp. 87-93. vol. 4, American Chemical Society.
Fluorous Technology in Discovery Applications, Fluorous Technologies, Inc., 2002-2003, http://fluorous.com/scavenging.html, 3 pages.
Louis Carpino, Principal Research Interests, Department of Chemistry—Faculty Research Areas—Louis Carpino, University of Massachusetts, http://www.chem.umass.edu/Carpino/carpino.html 2 pages.
Chemical Synthesis of Peptides, KVL, http://www.kemi.kvl.dk/~prh/html/research.htm, 9 pages.
Kung-Tsung Wang et al., Enhancement of Coupling Reaction in Peptide Synthesis by Microwave Irradiation, 12 pages, Published in 1992 and 1997.
Hui-Ming Yu et al., Enhanced Coupling Efficiency in Solid-Phase Peptide Synthesis by Microwave Irradiation, Journal of Organic Chemistry, vol. 57, No. 18, 1992, pp. 4781-4784, XP002299119.
Vincenzo Santagada et al., Microwave-Enhanced Solution Coupling of the Alpha, Alpha-dialkyl Amino Acid, Aib, Tetrahedron Letters, vol. 42, No. 31, Jul. 30, 2001, pp. 5171-5173, XP002299120.
M.C. Daga et al., Rapid Microwave-Assisted Deprotection of N-Cbz and N-Bn Derivatives, Tetrahedron Letters, Jul. 30, 2001 United Kingdom, vol. 42, No. 31, pp. 5191-5194, XP002299121.
J. M. Collins et al., Novel Method for Enhanced Solid Phase Peptide Synthesis Using Microwave Energy, Biopolymers, vol. 71, No. 3, 2003, p. 361, XP002299122.
Andrea Porcheddu et al., A New, Rapid, General Procedure for the Synthesis of Organic Molecules Supported on Methoxy-Polyethylene Glycol (MeOPEG) under Microwave Irradiation Conditions, Eur. J. Org. Chem. 2003, pp. 907-912.
Alexander Stadler et al., High-speed Couplings and Cleavages in Microwave-Heated, Solid-Phase Reactions at High Temperatures, Eur. J. Org. Chem. 2001, pp. 919-925.

(Continued)

*Primary Examiner* — Marcela M Cordero Garcia
(74) *Attorney, Agent, or Firm* — Summa, Additon & Ashe, P.A.

(57) ABSTRACT

A method is disclosed for carrying out peptide synthesis comprising deprotecting an Fmoc-protected amino acid with piperazine while applying microwave irradiation to the deprotection reaction.

17 Claims, 5 Drawing Sheets

OTHER PUBLICATIONS

Bruce Merrifield, Concept and Early Development of Solid-phase Peptide Synthesis, Methods Enzymol, 1997; 289: pp. 3-13.

Fernando Albericio et al., Coupling Reagents and Activation, Methods Enzymol, 1997; 289:104-126.

Overview of Peptide Synthesis. Anaspec. Accessed online Feb. 15, 2006 at http://www.anaspec.com/html/peptide_notes.html, pp. 1-11.

Kappe, Speeding Up Solid-Phase Chemistry by Microwave Irradiation. A Tool for High-Throughput Synthesis. American Laboratory, 2001, vol. 33, No. 10, pp. 13-16, 18-19.

Murray et al., Efficient Synthesis of a B-Peptide Combinatorial Library with Microwave-Irradiation. JACS. 2005, vol. 127, pp. 13271-13280.

Al-Obeidi, et al., apid Microwave-Assisted Solid-phase Synthesis (MASS): Parallel and Combinatorial Chemical Library Synthesis, Mini Reviews in Medicinal Chemistry. 2003, vol. 3, pp. 449-460.

Lew et al. Increasing Rates of Reaction: Microwave-Assisted Organic Synthesis for Combinatorial Chemistry. J. Comb Chem. Mar./Apr. 2002, vol. 4, No. 2, pp. 95-105.

Lange et al. Recent Advances in Microwave-Assisted Combinatorial Synthesis and Library Generation. Combinatorial Chemistry and High Throughput Screening. 2005, vol. 8, pp. 595-606.

Scharn et al. Spatially Addressed Synthesis of Amino- and Amino-Oxy-Substituted 1,3,5-Triazine Arrays on Polymeric Membranes. J. Comb Chem. 2000., vol. 2, pp. 361-369.

Scharn et al. Sequential Nucleophilic Substitution on Halogenated Triazines, Pyrimidines, and Purines: A Novel Approach to Cyclic Peptidomimetics. J. Org Chem. 2001, vol. 66, pp. 507-513.

* cited by examiner

Fmoc removal by Piperidine

Conventional SPPS of ACP Sequence [VQAAIDYING]

Microwave SPPS of [65-74]ACP Sequence [VQAAIDYING]

Aspartimide formation of Asp(X) sequences

20% Piperidine in DMF

Microwave SPPS of [Val-Tyr-Trp-Thr-Ser-Pro-Phe-Met-Lys-Leu-Ile-His-Glu-Gln-Cys-Asn-Arg-Ala-Asp-Gly-NH$_2$]; (SEQ ID NO: 1) 1=Product; 2=a and b-piperidides 20% Piperidine w/ 0.1M HOBt in DMF 5% Piperazine in DMF 5% Piperazine w/ 0.1M HOBt in DMF

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: Microwave assisted solid phase peptide
      synthesis

<400> SEQUENCE: 1
```

```
-continued

Val Tyr Trp Thr Ser Pro Phe Met Lys Leu Ile His Glu Gln Cys Asn
1               5                   10                  15

Arg Ala Asp Gly
            20

<210> SEQ ID NO 2
<211> LENGTH: 6
<212> TYPE: PRT
<213> ORGANISM: Artificial Sequence
<220> FEATURE:
<223> OTHER INFORMATION: Microwave assisted solid phase peptide
      synthesis

<400> SEQUENCE: 2

Val Lys Asp Gly Tyr Ile
1               5
```

MICROWAVE ENHANCED N-FMOC DEPROTECTION IN PEPTIDE SYNTHESIS

BACKGROUND

The present invention relates to microwave assisted chemistry and in particular relates to the chemistry of peptide synthesis, specifically the chemistry of the protection and deprotection steps in solid phase peptide synthesis ("SPPS").

A general background discussion of peptide synthesis, solid phase peptide synthesis and microwave assisted solid phase peptide synthesis is set forth in commonly assigned United States Patent Application Publication No. 20040260059, the contents of which are incorporated entirely herein by reference. Microwave enhancement of solid phase peptide synthesis is also commercially available in the form of the LIBERTY™ and DISCOVER® instruments available from CEM Corporation of Matthews, N.C., USA.

As further background, both three-letter and one-letter abbreviations are commonly used in this field to represent the 20 amino acids commonly found in proteins. In turn, groups or strings of these abbreviations are used to represent peptide chains. These abbreviations are widely used and recognized and will be understood in context when they appear herein.

As another detail, some sources prefer to refer to peptides as "polypeptides," and it will be understood that these terms are equivalent. The term peptide is used predominantly herein.

As set forth in the '059 publication and as well understood in this art, solid phase peptide synthesis is typically carried out by adding a first amino acid to a solid phase resin particle and then adding second and successive acids to the first acid to form the peptide chain. Attaching the growing chain to the solid phase resin particles permits the step-wise reactions to be carried out more easily.

In order to prevent undesired reactions at inappropriate times, each amino acid typically includes an intentionally-added composition referred to as a "protecting group" on the amino side of the molecule. Adding a second amino acid to the first amino acid accordingly requires removing the protecting group from the first acid. This step is referred to as "deprotection." Similarly (and successively), after the second acid and its protecting group have been added to the first acid, the protecting group must be removed from the second acid in order to add the third acid, and so forth.

As further known to those of skill in this art, the 9-fluorenylmethyloxycarbonyl group, commonly referred to as "N-Fmoc" (or simply "Fmoc") is a favored composition for acting as the protecting group in peptide synthesis, including (but not limited to) SPPS. Accordingly, the step of removing the Fmoc (deprotection) must be carried out repeatedly; i.e., every time another protected acid is added to the growing peptide chain.

During SPPS, the N-Fmoc protecting group can be removed by organic bases in a base-catalyzed elimination. Deprotection is most efficient with unhindered secondary amines, but is also susceptible to primary and tertiary amines. Typically a solution of 20% piperidine in DMF (N,N-dimethyl formamide) is used to form a dibenzofulvene (DBF) intermediate that is immediately trapped by the secondary amine to form an inert adduct.

For example, microwave-enchanced Fmoc deprotection was reported with 65-74ACP peptide. In this study complete deprotection was observed with 20% Piperidine in DMF in 1 minute. Without microwave multiple deletions were observed.

Piperidine has a favorable pKa (11.1), but because it is also a precursor for the synthesis of phenylcyclidine ("angel dust") it is regulated (in the U.S.) by the Drug Enforcement Agency. Piperidine is also toxic by ingestion and a strong irritant.

In difficult peptides incomplete Fmoc deprotection can be a problem and the use of the stronger tertiary base, 1,8-diazabicyclo[5.4.0]undec-7-ene (DBU) has been shown to increase reaction efficiency. Typically, small amounts of piperidine are added to DBU to scavenge the free DBF because DBU alone does not accomplish this. If not scavenged, free DBF can potentially react with the resulting resin-bound terminal Nα-amine preventing acylation of the next amino acid.

The deprotection reaction is often performed in two stages to prevent such DBF alkylation of the resin-bound terminal Nα-amine. The first stage is typically shorter than the second and serves to remove a significant amount of DBU from the reaction vessel before a longer deprotection reaction is employed with fresh reagent.

Base catalyzed aspartimide formation (described in detail in the literature) also can be a serious problem during peptide synthesis chain assembly. In this side reaction the nitrogen atom attached to the α-carboxy group of either aspartic acid or asparagine attacks the side chain ester or amide group, respectively. Nucleophilic attack then causes subsequent ring opening, which gives rise to a mixture of α-aspartyl and β-aspartyl peptides.

Aspartimide formation has been shown to occur in sequences containing the "Asp-X" moiety, where X=[Gly, Asn, Ser, Thr]. This sequence is diagrammed in FIG. 4. Each subsequent deprotection cycle after the "Asp-X" sequence further increases aspartimide formation. This can be a serious problem in longer peptides with multiple Asp residues.

This process naturally occurs in biological systems with proteins containing aspartic acids. Including the β-tert-butyl ester protection is thought to reduce this because of its bulkiness. This side reaction is, however, well documented in routine peptide synthesis even with side chain protection of aspartic acid. Incorporation of 0.1 M HOBt (hydroxybenzotriazole) in the deprotection solution has been shown to reduce aspartimide formation[1,2]. In many cases, however, this still leads to significant levels of aspartimide. The hexapeptide "VKDGYI" (SEQ ID NO: 2) has been shown to produce significant amounts of aspartimide related products during SPPS. This peptide was synthesized in a single-mode microwave manually with three 30-second 100 W cycles with ice bath cooling between each irradiation cycle. Maximum temperature was measured to be around 40° C. Significant aspartimide formation was detected using a 20% Piperidine in DMF solution. This was reduced with alterations in the deprotection solution, but only completely eliminated with use of an Hmb (hydroxyl-4-methoxybenzyl) dipeptide insertion of DG.

Table 1 illustrates the effect of deprotection reagent on aspartimide formation of VKDGYI (SEQ ID NO: 2)

| Deprotection Reagent | % Aspartimide |
| --- | --- |
| 20% Piperidine in DMF | 10.90 |
| 20% Piperidine w/ 0.1M HOBt in DMF | 5.55 |
| Hexamethyleneimine/N-ethylpyrrolidine/HOBt in NMP/DMSO | 1.49 |
| 20% Piperidine in DMF (w/HMB backbone protection) | Not detected |

Accordingly, given some of the practical disadvantages of piperidine and the potential side reactions, an opportunity exists for improving deprotection chemistry in SPPS.

SUMMARY

The invention is a method of carrying out peptide synthesis comprising deprotecting an Fmoc-protected amino acid with piperazine while applying microwave irradiation to the deprotection reaction.

The foregoing and other objects and advantages of the invention and the manner in which the same are accomplished will become clearer based on the followed detailed description taken in conjunction with the accompanying drawings.

DETAILED DESCRIPTION

Figure 1:
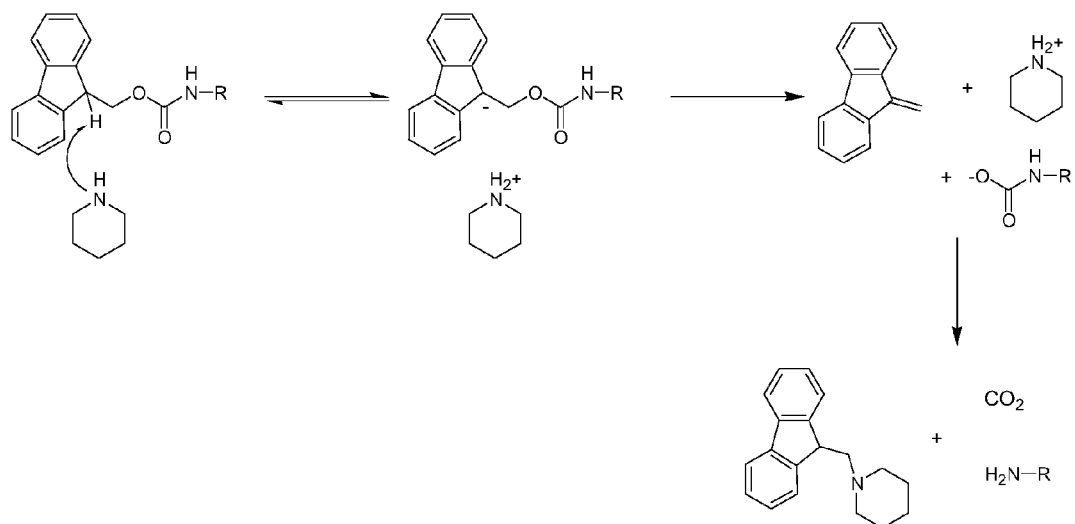
FIG. 1 illustrates the reactions scheme for Fmoc removal by piperidine.
Figure 2:
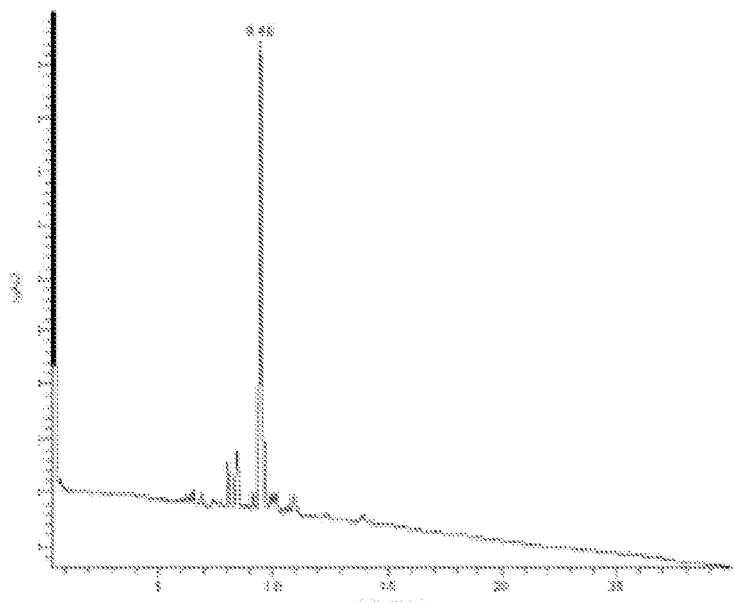
FIG. 2 is a liquid chromatography fraction graph for a conventional solid phase synthesis using piperidine.
Figure 3:
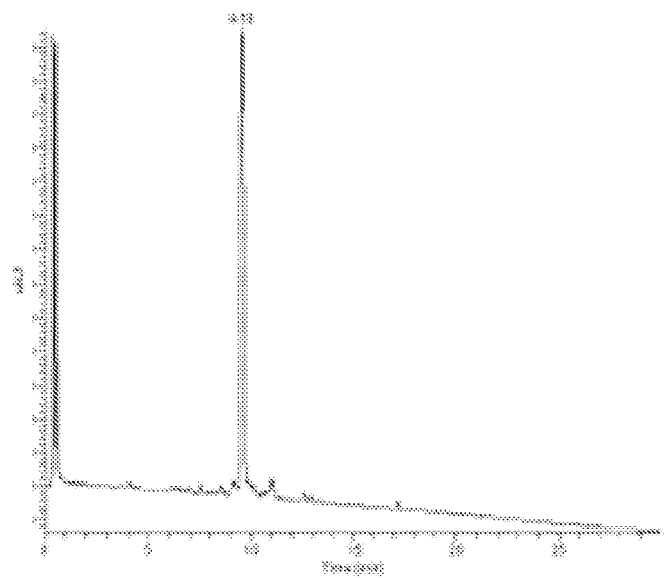
FIG. 3 is a liquid chromatography fraction graph for microwave assisted solid phase synthesis of the same sequence represented by FIG. 2.
Figure 4:
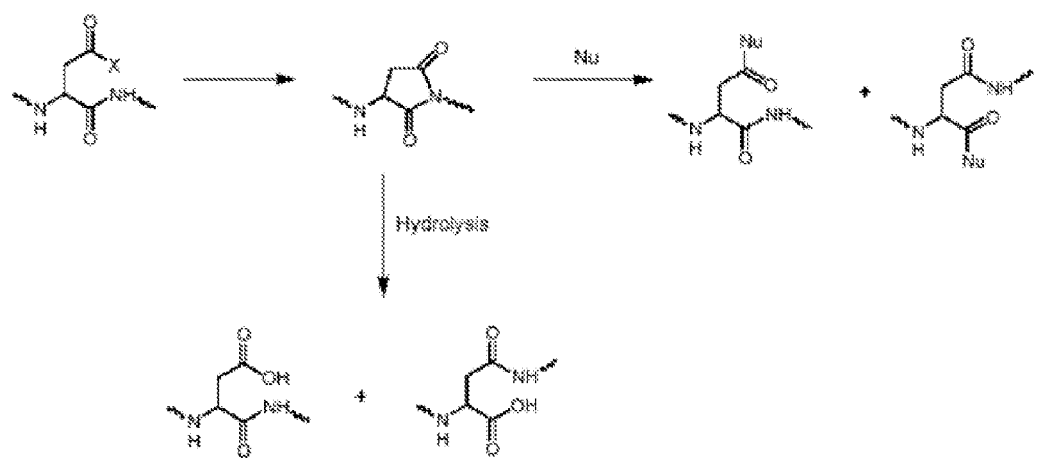
FIG. 4 illustrates aspartimide formation of Asp(X) sequences.
Figure 5:
FIG. 5 illustrates the ring diagram formulas for piperidine and piperazine.
Figure 6:
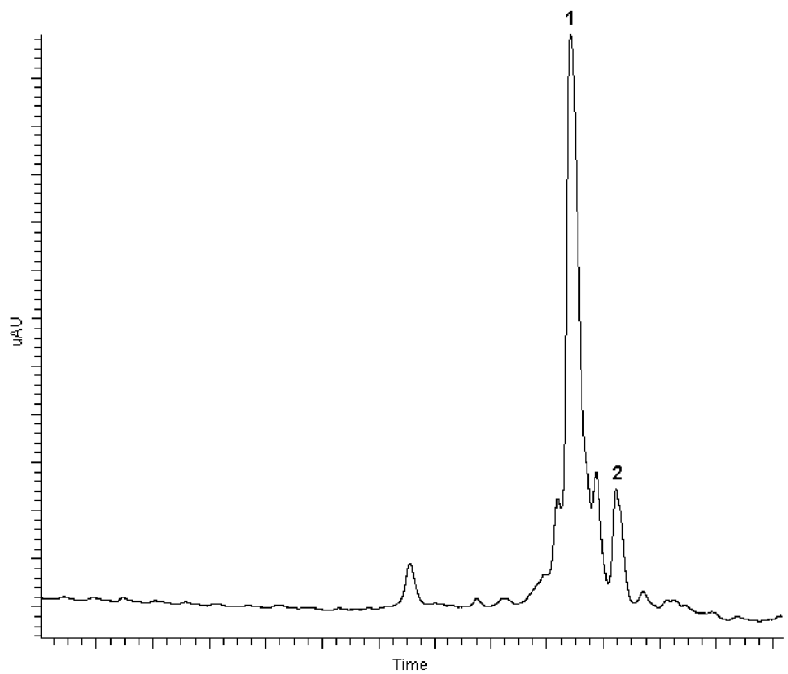
FIG. 6 is a microwave assisted solid phase synthesis liquid chromatography fraction.
Figure 7:
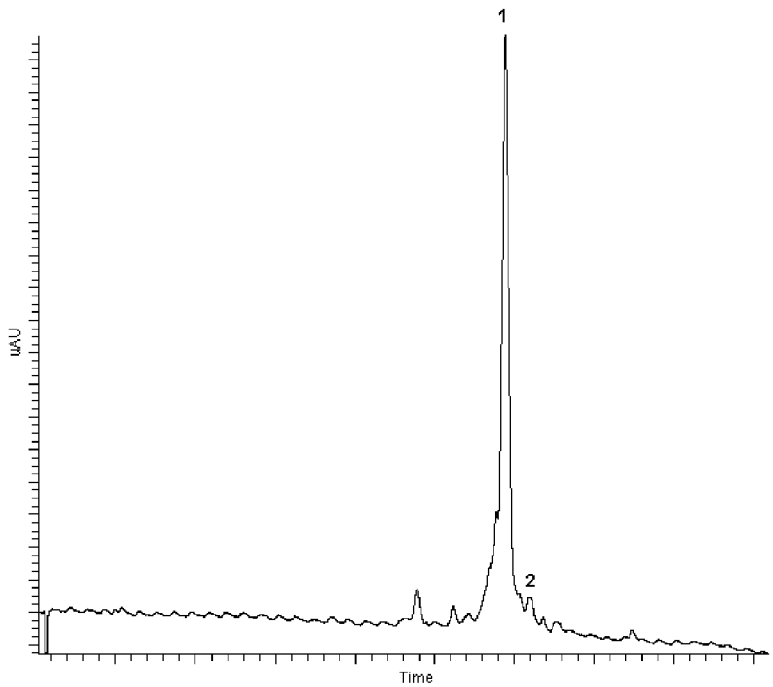
FIG. 7 is a liquid chromatography fraction graph for the same reaction as illustrated in FIG. 6 but with 0.1M HOBt in DMF.
Figure 8:
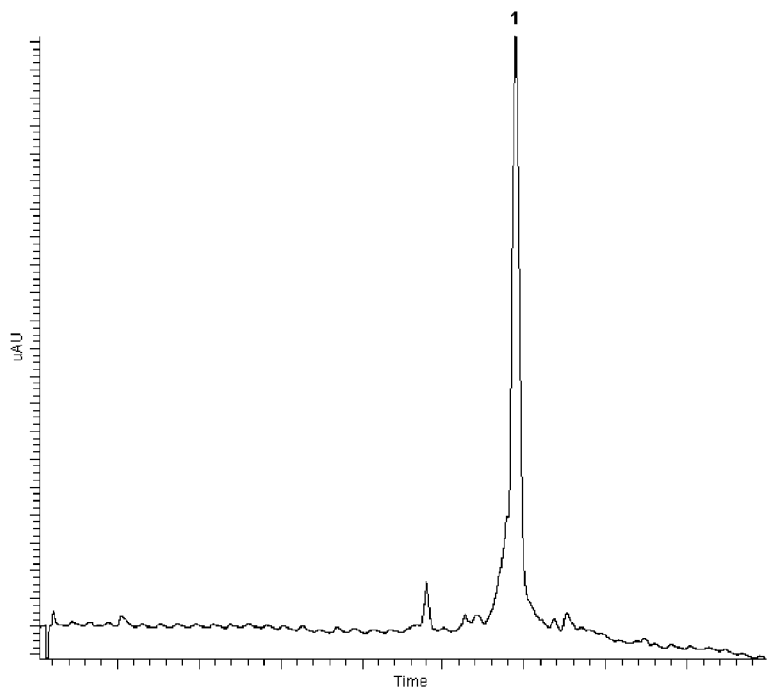
FIG. 8 is a liquid chromatography fraction graph for the same reaction as FIGS. 6 and 7 but using five percent piperazine in DMF.
Figure 9:
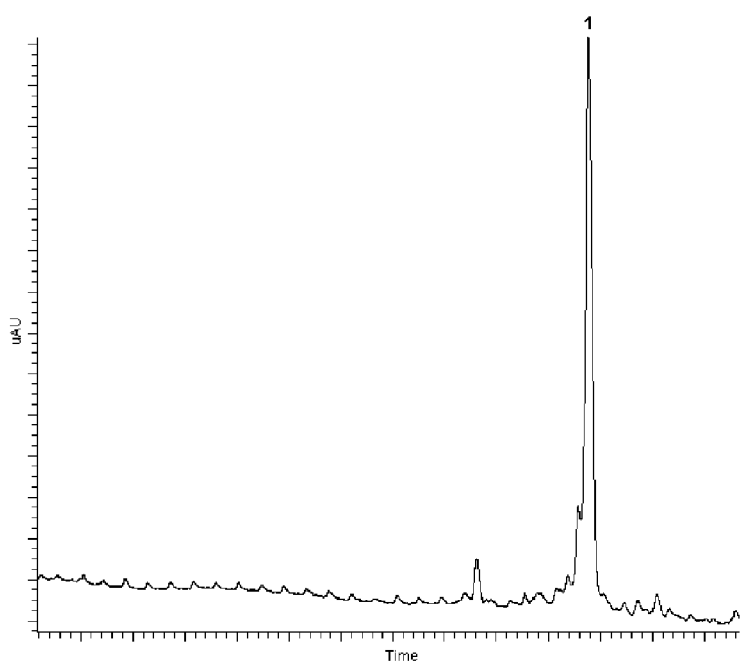
FIG. 9 is yet another liquid chromatography fraction graph for the same reaction but using five percent piperazine in 0.1M HOBt in DMF

The use of piperazine in place of piperidine (both formulas illustrated in FIG. 5) has demonstrated significantly lower levels of aspartimide formation. In comparison, piperazine is a non-controlled substance that makes it more accessible to laboratories than piperidine. In addition, piperazine is an oral medication used to treat roundworm infection and is less odourous and toxic than piperidine. Piperazine, however, has a pKa of 9.8 compared to 11.1 for piperidine and is thus a slower deprotection reagent in conventional schemes. As a result, during conventional synthesis of hydrophobic sequences the use of piperazine can lead to more incomplete Fmoc removal. Often DBU is used as a stronger deprotection agent than piperidine, but can generate high levels of aspartimide formation.

In the invention, microwave energy is used to substantially accelerate Fmoc deprotection with piperazine. Complete Fmoc removal can be accomplished with piperazine in 3 minutes. This allows for an efficient deprotection reaction with a very desirable reagent. Aspartimide formation was minimized on a 20mer peptide with a "Gly-Asp" C-terminal sequence. Fmoc removal was performed under a range of deprotection solutions with a 0:30, followed by 3:00 method with maximum temperature reaching 80° C.

FIGS. 6-9 illustrate comparator results of microwave SPPS of [Val-Tyr-Trp-Thr-Ser-Pro-Phe-Met-Lys-Leu-Ile-His-Glu-Gln-Cys-Asn-Arg-Ala-Asp-Gly-NH2 (SEQ ID NO: 1)]. In the figures the numeral 1 designates product and the numeral 2 designates alpha and beta peptides. As indicated by the captions, conditions were as noted immediately above, with the reactions differing with respect to piperidine, piperazine, and the presence or absence of HOBt in conjunction with DMF.

Deprotection with piperazine showed an overall reduction in aspartimide formation side-products. A reduction in aspartimide formation was observed with piperazine compared to piperidine. In both cases, addition of 0.1M HOBt reduced aspartimide formation further. With piperidine containing deprotection solutions, α and β piperidides resulting from base catalyzed imide ring opening were present on liquid chromatography/mass spectrometry analysis. Coresponding products with piperazine containing deprotection solutions were not detected. Additionally, racemization of the aspartic acid that can occur through hydrolysis of the imide ring in solution was measured to be significantly significantly less with piperazine in place of piperidine.

Table 2 lists the % D-Asp measured by GC/MS after hydrolysis with 6N DC1/D2O

| Deprotection Reagent | % Aspartimide | % D-Asp |
| --- | --- | --- |
| 20% Piperidine in DMF | 31.50 | 9.60 |
| 20% Piperidine w/ 0.1M HOBt in DMF | 9.10 | 3.83 |
| 5% Piperazine w/ 0.1M HOBt in DMF | 3.15 | 1.18 |

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of carrying out solid phase peptide synthesis including deprotecting, activating, coupling and cleaving steps comprising:
    deprotecting an Fmoc-protected amino acid with piperazine while applying microwave irradiation to the deprotection reaction; and
    applying microwave energy while carrying out the cleaving step.

2. A method according to claim 1 comprising applying microwave energy while carrying out the activating and coupling steps of peptide synthesis.

3. A method according to claim 2, comprising repeating the deprotecting, activating, and coupling cycle to add successive acids to form a peptide of a desired sequence.

4. A method according to claim 1, comprising proactively cooling the reaction during the application of microwave energy to thereby prevent undesired degradation of the peptide or acids by limiting heat accumulation that would otherwise result from the application of the microwave energy.

5. A method according to claim 1 comprising monitoring the temperature of the vessel and moderating the applied power based upon the monitored temperature.

6. A method according to claim 3, comprising repeating the deprotecting, activating, and coupling cycle to add successive acids to form at least a decamer-peptide.

7. A method according to claim 3, comprising repeating the deprotecting, activating, and coupling cycle to add successive acids to form at least a 20mer-peptide.

8. A method of avoiding unwanted side reactions during a solid phase peptide synthesis comprising deprotecting, activating, coupling and cleaving steps,
    wherein the deprotecting step includes deprotecting an Fmoc-protected amino acid with piperazine while applying microwave irradiation to the deprotection reaction; and carrying out the deprotecting step in three minutes or less; and
    wherein the cleaving step comprises applying microwave energy while carrying out the cleaving step.

9. A method according to claim 8, further comprising applying-microwave energy while carrying out the activating and coupling steps of the solid phase peptide synthesis.

10. A method according to claim 8, comprising repeating the deprotecting, activating, and coupling cycle to add successive acids to form a peptide of a desired sequence.

11. A method according to claim 8, further comprising proactively cooling the reaction during the application of microwave energy to thereby prevent undesired degradation of the peptide or acids by limiting heat accumulation that would otherwise result from the application of the microwave energy.

12. A method according to claim 8, further comprising monitoring the temperature of the synthesis reaction and moderating the applied power based upon the monitored temperature.

13. A method according to claim 8, wherein said deprotecting step comprises applying microwave irradiation for 30 seconds, followed by applying microwave irradiation for three minutes.

14. A method according to claim 13, wherein said deprotecting step is conducted at a maximum temperature of 80° C.

15. A method of carrying out peptide synthesis comprising:
    deprotecting an Fmoc-protected amino acid with piperazine while applying microwave irradiation to the deprotection reaction and proactively cooling the reaction during the application of microwave energy to thereby prevent undesired degradation of the peptide or amino acids by limiting heat accumulation that would otherwise result from the application of the microwave energy.

16. A method of carrying out peptide synthesis comprising:
    deprotecting an Fmoc-protected amino acid with piperazine and hydroxybenzotriazole (HOBt) while applying microwave irradiation to the deprotection reaction.

17. A method according to claim 8, wherein said deprotecting step comprises deprotecting an Fmoc-protected amino acid with piperazine and hydroxybenzotriazole (HOBt) while applying microwave irradiation to the deprotection reaction.

* * * * *